(12) United States Patent  (10) Patent No.: US 8,614,353 B2
Catozzi et al.  (45) Date of Patent: Dec. 24, 2013

(54) PROCESS FOR PREPARING CINACALCET

(75) Inventors: Nicola Catozzi, Isola Vicentina (IT);
Johnny Foletto, Arcole (IT);
Massimiliano Forcato, Galzignano Terme (IT); Roberto Giovanetti, Schio (IT); Giorgio Soriato, Caldiero (IT); Massimo Verzini, Caldiero (IT)

(73) Assignee: Zach System S.p.A., Bresso (Milan) (IT)

( * ) Notice: Subject to any disclaimer, the term of this patent is extended or adjusted under 35 U.S.C. 154(b) by 129 days.

(21) Appl. No.: 13/126,609

(22) PCT Filed: Oct. 16, 2009

(86) PCT No.: PCT/EP2009/063603
§ 371 (c)(1),
(2), (4) Date: Apr. 28, 2011

(87) PCT Pub. No.: WO2010/049293
PCT Pub. Date: May 6, 2010

(65) Prior Publication Data
US 2011/0207965 A1 Aug. 25, 2011

(30) Foreign Application Priority Data
Oct. 28, 2008 (EP) .................................. 08167762

(51) Int. Cl.
*C07C 221/00* (2006.01)
*C07C 223/00* (2006.01)
*C07C 225/00* (2006.01)
*C07C 211/00* (2006.01)

(52) U.S. Cl.
USPC ............................ 564/343; 564/336; 564/387

(58) Field of Classification Search
None
See application file for complete search history.

(56) References Cited

U.S. PATENT DOCUMENTS

2007/0259964 A1 11/2007 Lifshitz-Liron

OTHER PUBLICATIONS

Thiel, O et al. Tetrahedron Letters 49 (2008) 13-15 (available online Nov. 26, 2007).*

* cited by examiner

*Primary Examiner* — Clinton Brooks
(74) *Attorney, Agent, or Firm* — Lucas & Mercanti, LLP

(57) ABSTRACT

A process for preparing N-[(1R)-1-(1-naphthyl)ethyl]-3-[3-(trifluoromethyl)-phenyl]propan-1-amine of formula (I) i.e. Cinacalcet and its intermediates of formulae (V), (Va) and (Vb).

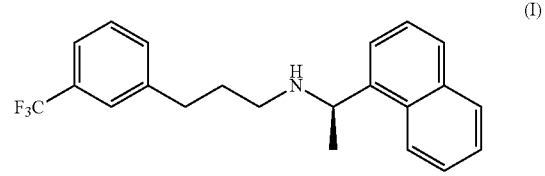

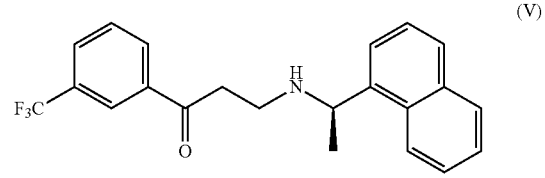

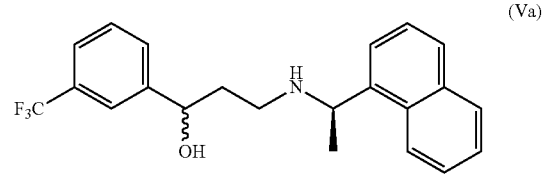

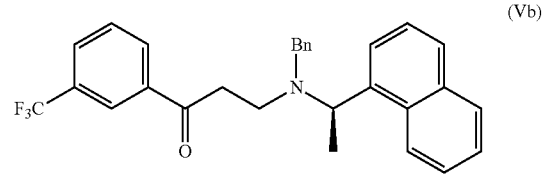

14 Claims, No Drawings

PROCESS FOR PREPARING CINACALCET

This application is a U.S. national stage of PCT/EP2009/063603 filed on Oct. 16, 2009 which claims priority to and the benefit of European Application No. 08167762.7 filed on Oct. 28, 2008, the contents of which are incorporated herein by reference.

The invention relates to a process for preparing the active product ingredient Cinacalcet, its intermediates and its pharmaceutically acceptable salts, especially the hydrochloride salt.

Cinacalcet (CNC), namely N-[(1R)-1-(1-naphthyl)ethyl]-3-[3-(trifluoromethyl)-phenyl]propan-1-amine of formula (I)

(I)

is used in therapy as hydrochloride salt.

The hydrochloride salt of Cinacalcet (CNC.HCl), marketed as MIMPARA™ in the European Union, is a calcimimetic agent that decreases the secretion of parathyroid hormone by activating calcium receptors.

MIMPARA™ is approved for the treatment of secondary hyperparathyroidism (SHPT) in patients with chronic kidney disease receiving dialysis and for the treatment of primary hyperparathyroidism (PHPT) in patients for whom parathyroidectomy is not clinically appropriate or contraindicated.

U.S. Pat. No. 6,011,068 discloses a class of arylalkylamines comprising generically Cinacalcet and salts thereof.

U.S. Pat. No. 6,211,244 describes specifically Cinacalcet or a pharmaceutically acceptable salt or complex thereof as the compound 22J. U.S. Pat. No. 6,211,244 also discloses synthetic methods for preparing calcium receptor-active molecules, such a those having analogue structure of Cinacalcet, by a reductive amination approach comprising the condensation of the appropriate aromatic aldehyde or ketone with the suitable aryl amine followed by reduction with sodium cyanoborohydride (NaBH₃CN) or sodium triacetoxyborohydride, or by a diisobutyl aluminium hydride (DIBAL-H) mediated condensation of an aromatic amine with an aryl nitrile, followed by the reduction of the intermediate aluminium-imine complex with sodium cyanoborohydride or sodium borohydride. The method for condensing a nitrile with a primary or a secondary amine in the presence of diisobutyl aluminium hydride to form the corresponding imine was generically disclosed in the U.S. Pat. No. 5,504,253.

The preparation of Cinacalcet, described in Scheme 1 of *Drugs of the Future* 2002, 27(9), 831-836, (2002), comprises the reaction of 1(R)-(1-naphthyl)ethylamine (R-NEA) with 3-[3-(trifluoromethyl)phenyl]propionaldehyde by means of titanium tetraisopropoxide (Ti(O-i-Pr)₄) to give the corresponding imine, which is finally reduced with sodium cyanoborohydride in ethanol, as depicted in the following Scheme 1:

Scheme 1

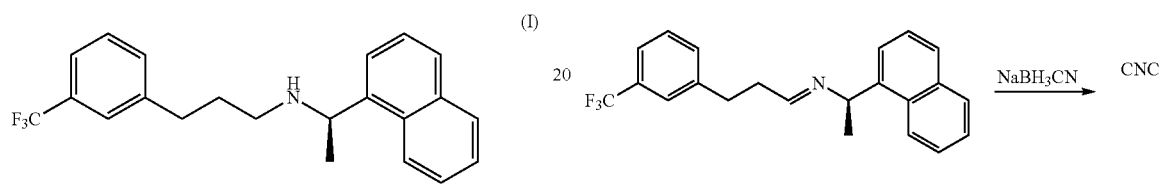

*Tetrahedron letters*, (45), 8355-8358, (2004) footnote 12, discloses the preparation of the starting material 3-[3-(trifluoromethyl)phenyl]propionaldehyde by reduction of 3-(trifluoromethyl)cinnamic acid to the corresponding alcohol followed by oxidation to give the desired aldehyde, as depicted in the following Scheme 2:

Scheme 2

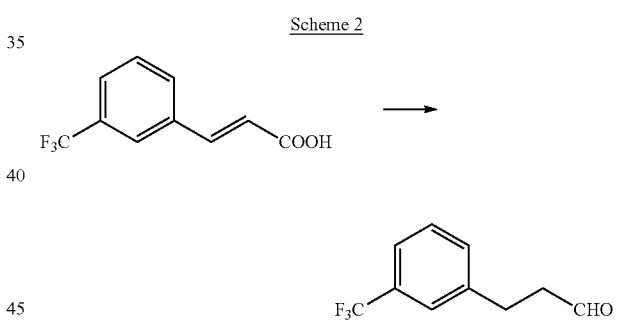

According to *Synthetic Communications*, 38: 1512-1517 (2008), the above synthesis of Cinacalcet involves the use of reagents such as Ti(O-i-Pr)₄ and DIBAL-H, which have to be handled in large volumes because the Cinacalcet has to be prepared on commercial scale and the handling of this moisture-sensitive and pyrophoric reagents on a large scale makes the synthesis more strenuous.

International patent application WO 2008/035212 discloses an alternative process for preparing 3-[3-(trifluoromethyl)phenyl]propionaldehyde, which comprises the oxidation of 3-[3-(trifluoromethyl)phenyl]propan-1-ol.

U.S. Pat. No. 7,250,533 discloses another process for preparing Cinacalcet, which comprises converting the hydroxyl moiety of 3-[3-(trifluoromethyl)phenyl]propanol into a good leaving group and combining the resulting compound with (R)-(1-naphthyl)ethylamine preferably in the presence of a base, according to the following Scheme 3:

Scheme 3

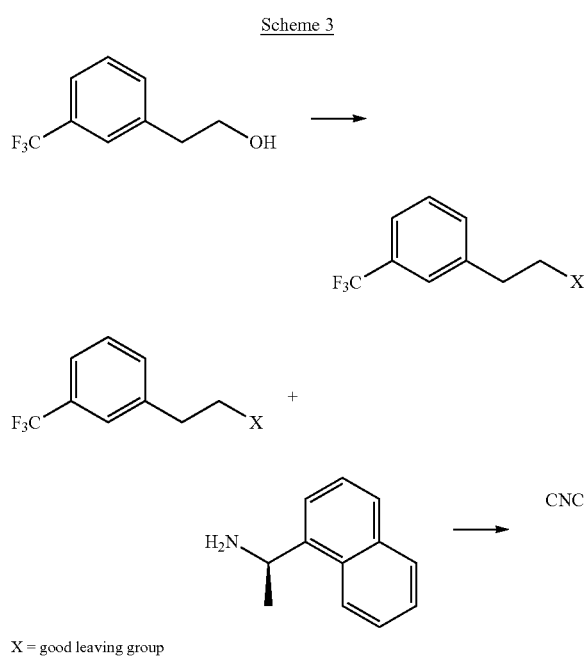

X = good leaving group

According to U.S. Pat. No. 7,294,735, Cinacalcet carbamate may be formed in various amounts while using different solvents during the synthesis of Cinacalcet as described in the above U.S. Pat. No. 7,250,533. U.S. Pat. No. 7,294,735 discloses a process for the preparation of Cinacalcet hydrochloride, containing Cinacalcet carbamate in an amount of about 0.03 area percent to about 0.15 area percent as measured by a chromatographic method, comprising the steps of (a) dissolving Cinacalcet, containing Cinacalcet carbamate in an amount of about 3 area percent to about 6 area percent as determined by a chromatographic method, in acetone, a linear or a branch-chain $C_{2-8}$ ether, mixtures thereof or with water; (b) adding hydrogen chloride to obtain a precipitate; and (c) recovering the Cinacalcet hydrochloride.

US patent application No. 2007/259964 provides a process for preparing Cinacalcet comprising reducing 3-(trifluoromethyl)cinnamic acid to obtain 3-(3-trifluoromethylphenyl)-propanoic acid, optionally converting 3-(3-trifluoromethylphenyl)-propanoic acid into a suitable acid derivative and combining the 3-(3-trifluoromethylphenyl)-propanoic acid or, if the case, said derivative with (R)-(1-naphthyl)ethylamine to give (R)—N-(1-(naphthalen-1-yl)ethyl)-3-(3-(trifluoromethyl)phenyl)propanamide and reducing (R)—N-(1-(naphthalen-1-yl)ethyl)-3-(3-(trifluoromethyl)phenyl) propanamide to Cinacalcet, according to the following Scheme 4:

Scheme 4

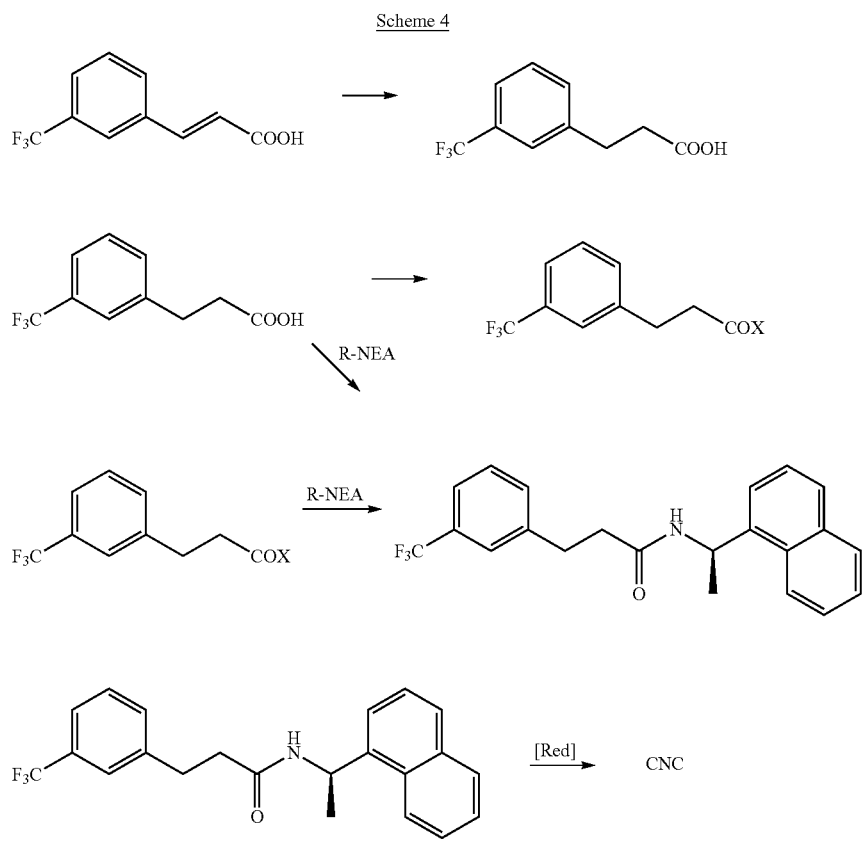

X = carboxyl, alkoxy, halogen or sulfonyl

*Tetrahedron letters*, (49), 13-15, (2008), discloses a synthetic sequence to Cinacalcet hydrochloride comprising reduction of 3-(trifluoromethyl)cinnamic acid in the presence of palladium hydroxide to obtain 3-(3-trifluoromethylphenyl)-propanoic acid, which is coupled with (R)-1-(1-naphthyl)ethylamine to the corresponding amide. The amide is then reduced in the presence of boron trifluoride-THF and sodium borohydride as reducing agents. After complete conversion, the resulting amine-borane complex is hydrolyzed by the addition of water and the crude Cinacalcet extracted into toluene is reacted with hydrochloric acid to give Cinacalcet hydrochloride, according to the following Scheme 5:

Scheme 5

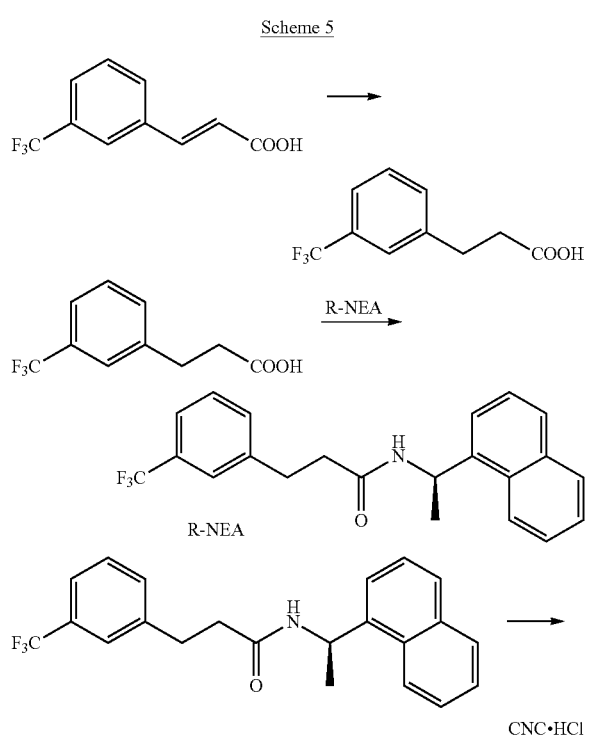

In patent application No. 2007MU00555 and *Synthetic Communications*, 38: 1512-1517 (2008) is disclosed another process for preparing Cinacalcet hydrochloride, via (R)—N-(1-(naphthalen-1-yl)ethyl)-3-(3-(trifluoromethyl)phenyl)propanamide.

U.S. Pat. No. 7,393,967 discloses a process for preparing Cinacalcet via coupling of 3-bromotrifluorotoluene with allylamine (R)—N-(1-(naphthalen-1-yl)ethyl)prop-2-en-1-amine in the presence of a catalyst and at least one base to obtain (R,E)-N-(1-(naphthalen-1-yl)ethyl)-3-(3-(trifluoromethyl)phenyl)prop-2-en-1-amine (CNC-ene) and reducing the unsaturated Cinacalcet to obtain Cinacalcet, as depicted in the following Scheme 6:

Scheme 6

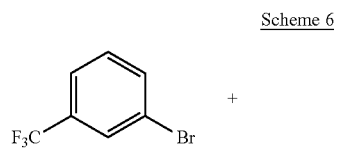

-continued

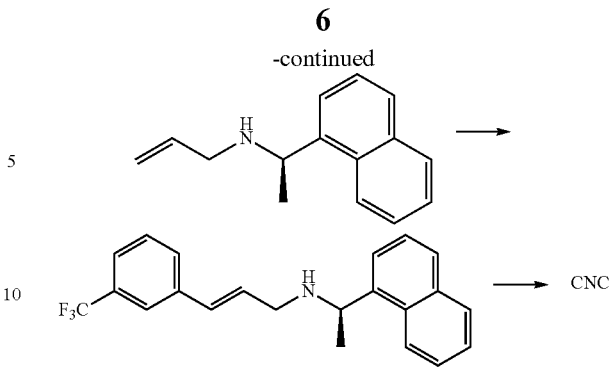

The present invention provides a novel and efficient process that leads to Cinacalcet, its pharmaceutically acceptable salts and intermediates thereof, which is convenient for the industrial scale and provides the desired product in good yields. In particular, the inventors found that the complete scaffold of Cinacalcet can be build up in one or few synthetic steps, which comprise a multi-component Mannich-type reaction, starting from commercial, readily available, cheap and safe starting materials.

Accordingly, it is an object of the present invention to provide a method for preparing Cinacalcet and its salts, particularly the hydrochloride salt, and intermediates thereof, which can be used for mass production.

In one embodiment, the present invention provides a process for the preparation of Cinacalcet intermediate of formula (V)

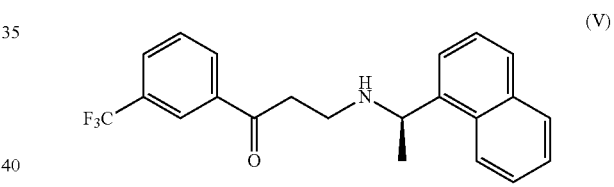

comprising the step of:

a) reacting 3-(trifluoromethyl)acetophenone of formula (II)

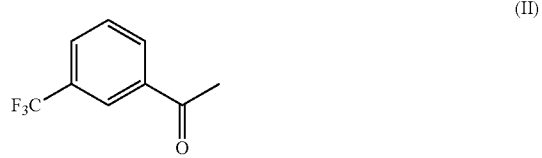

with (R)-(1-naphthyl)ethylamine of formula (III)

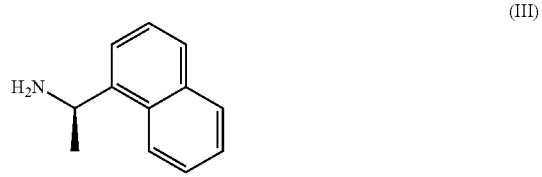

in the presence of formaldehyde.

Alternatively, the present invention provides a process for the preparation of the compound of formula (V), comprising the steps of:

b) reacting the compound of formula (II) as defined above
(i) with a compound of formula,

wherein $R_1$ and $R_2$ represent, independently, hydrogen or $C_1$-$C_5$ alkyl, provided that when one of $R_1$ and $R_2$ is hydrogen, the other is not hydrogen; or wherein $R_1$ and $R_2$ together form a $C_4$-$C_7$-alkylene bridge, so that with the inclusion of the nitrogen atom to which they are linked form a heterocycle, wherein one —$CH_2$— group of the $C_4$-$C_7$-alkylene bridge, can be replaced by —O—, in the presence of formaldehyde; or
(ii) with a N-methyl-N-methylenemethanaminium halide of formula

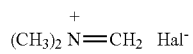

wherein Hal is a halogen atom,
to obtain the compound of formula (IV)

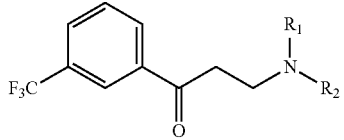

wherein $R_1$ and $R_2$ are as defined above;
c) alkylating the compound of formula (IV) with an alkylating agent selected from the group of compounds of formula: $R_3$—X, $CO(OR_3)_2$, $SO_2(OR_3)_2$, $PO(OR_3)_3$, $CH_3PO(OR_3)_2$ and $(4\text{-}NO_2C_6H_4O)PO(OR_3)_2$, wherein $R_3$ is $C_1$-$C_4$alkyl and X is I, Br, $OSO_2CF_3$ or $OSO_2F$, to obtain a compound of formula (IVa)

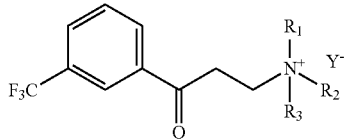

wherein Y=X as defined above or $R_3OCO_2$, $R_3OSO_3$, $(R_3O)_2PO_2$, $CH_3PO_2OR_3$, $(4\text{-}NO_2\text{—}C_6H_4O)PO_2OR_3$; and
d) coupling a compound of formula (IVa) with (R)-(1-naphthyl)ethylamine of formula (III).

The compound of formula (V) can then be used for preparing Cinacalcet.

The term $C_1$-$C_n$ alkyl, wherein n may have a value from 1 to 5, represents a saturated, linear or branched hydrocarbon chain with 1 to n carbon atoms and which is attached to the rest of the molecule by a single bond. Examples of such groups include methyl, ethyl, n-propyl, 1-methylethyl (isopropyl), n-butyl, n-pentyl, 1,1-dimethylethyl (t-butyl), and the like.

In a preferred aspect of the present invention, formaldehyde reagent is provided as paraformaldehyde.

When, in a compound of formula $HNR_1R_2$, $R_1$ and $R_2$ and $R_2$ represent, independently, hydrogen or $C_1$-$C_5$alkyl, $R_1$ and $R_2$ can not be hydrogen at the same time.

When, in a compound of formula $HNR_1R_2$, $R_1$ and $R_2$ are taken together with the nitrogen atom to which they are linked to form a heterocycle, wherein one —$CH_2$— group of the $C_4$-$C_7$-alkylene bridge, can be replaced by —O—, the formed heterocycle is pyrrolidine, piperidine, oxazolidine or morpholine, preferably morpholine.

A halogen atom Hal is Cl, Br, F or I, preferably I.

According to the invention, the Mannich-type reaction is preferably employed to achieve the formaldehyde-mediated condensation of the ketone moiety of formula (II) and the secondary amine of formula (III) by means of a methylene bridge. Typically, when performing the said coupling reaction under the above step a), the hydrochloride salt of the amine of formula (III), which exists in equilibrium with the free amine, is used. Particularly, the Mannich-type reaction under step a) can be carried out in acidic medium, for example with an acid selected from HBr, sulphuric acid, HCl and methansulphonic acid, preferably HCl or methansulphonic acid, mixing the reactants in a solvent that can be selected from water, acetonitrile, a linear or branched $C_1$-$C_5$ alcohol, such as, for example methyl, ethyl, n-propyl, iso-propyl, n-butyl, sec-butyl or tert-butyl alcohol, methyl isobutyl ketone (MIBK) and dioxane; preferably, the reactants are mixed in an high boiling alcohol, for example, sec-butyl alcohol, or in neat conditions, i.e. without solvent. The reaction is carried out at refluxing temperature of the selected solvent that can vary from 25° to 150° C., for about 1 to about 90 hours, depending on the solvent. The compound of formula (V) is then precipitated from the reaction medium by cooling or by addition of an anti-solvent chosen from a linear or cyclic $C_4$-$C_8$ ether such as, for example 1,2-dimethoxyetane, 2-methoxyethyl ether, diisopropyl ether, dibutyl ether, methyl tert-butyl ether, tetrahydrofuran (THF) or 1,4-dioxane, a linear or branched $C_5$-$C_8$ cyclic or aromatic hydrocarbons, such as, for example pentane, hexane, heptane, cyclohexane, isooctane, toluene or xylene, preferably toluene; or the compound of formula (V) is extracted with a suitable organic solvent such as, for example a $C_4$-$C_8$ ether as defined above, ethyl acetate (EtOAc), DCM or toluene, preferably toluene.

Alternatively, the formaldehyde-mediated Mannich-condensation can be employed to form the Mannich base of formula (IV), by coupling the compound of formula (II) with a suitable compound of formula $HNR_1R_2$ as defined under (i) in the above step b), operating at a temperature between 25° and 120° C., depending on the solvent that can be selected from water, acetonitrile, a linear or branched $C_1$-$C_5$ alcohol as defined above, MIBK and dioxane, more preferably the solvent is an high boiling alcohol, for example sec-butyl alcohol. The Mannich base of formula (IV) can also be obtained by reacting the compound of formula (II) with N-methyl-N-methylenemethanaminium halide (Eschenmoser's salt), preferably iodide, as defined under (ii) in step b), operating in acidic medium, for example with an acid selected from HBr, sulphuric acid, HCl and methansulphonic acid, preferably HCl or methansulphonic acid, mixing the reactants in a solvent that can be selected from water, acetonitrile, a linear or branched $C_1$-$C_5$ alcohol as defined above, MIBK and dioxane; more preferably, the reactants are mixed in an high boiling alcohol, for example, sec-butyl alcohol, or in neat conditions, i.e. without solvent. The reaction is carried out at refluxing temperature of the selected solvent that can vary from 25° to 150° C., for about 1 to about 90 hours, depending on the solvent.

The alkylating reaction performed under step c) can be carried out at a temperature between 0° and 80° C. Typically, the reaction runs at a temperature between 25° C. to 40° C. and proceeds to completion within about 1 to 48 hours. Preferably, the alkylating agent is a compound of formula $R_3X$ as defined above wherein X is preferably I, more preferably the compound of formula $R_3X$ is $CH_3I$.

The coupling reaction performed under step d) can be carried out in an organic solvent selected from EtOAc, dimethylformamide, acetonitrile and toluene, preferably acetonitrile or toluene and more preferably toluene, optionally in the presence of a suitable organic base including an alkali metal carbonate or hydroxide, for example calcium carbonate, potassium carbonate, sodium carbonate, sodium hydroxide or potassium hydroxide, preferably sodium or potassium carbonate, and a $C_1$-$C_5$ alkylamine, for example triethylamine or diisopropylethylamine, at a temperature between 0 to 80° C., over a period of about 2 to 24 hours.

For clarity's sake, the above process may be illustrated by the following Scheme 7:

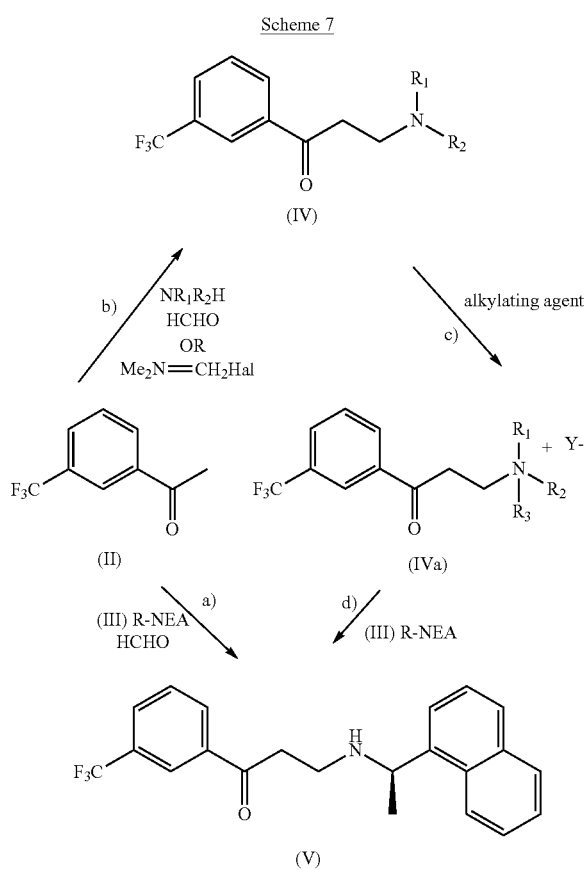

In another embodiment, the present invention encompasses a process for preparing Cinacalcet, by preparing a compound of formula (V) as described above, and converting it to Cinacalcet.

In another embodiment, the present invention provides the preparation of a Cinacalcet intermediate of formula (Va)

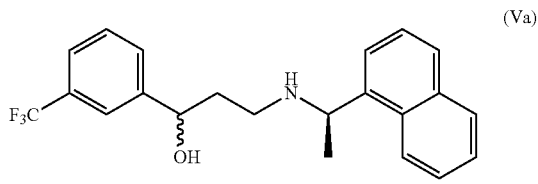 [SMILES: C[C@@H](NCCC(O)c1cccc(C(F)(F)F)c1)c1cccc2ccccc12]

which comprises the step of:
e) reducing the compound of formula (V) in the presence of a reducing agent or by mean of a catalytic hydrogenation process.

The compound of formula (Va) is obtained under step e) as a diastereoisomeric mixture, i.e. as a mixture of (R)- and (S)-3-((R)-1-(naphtalen-1-yl)ethylamino-1-(3-(trifluoromethyl)phenyl)propan-1-ol.

Suitable reducing agents include sodium borohydride, lithium borohydride, diisobutyl aluminium hydride and 1,1,3,3-tetramethyldisiloxane in combination with a Lewis acid. Suitable reduction catalysts to be used with gaseous hydrogen, include Pd/C, $PtO_2$ (Adam's catalysts), Raney nickel or $PdCl_2$. The reaction under step e) can be carried out in a solvent selected from, for example water, a $C_1$-$C_4$ alcohol as defined above, a $C_4$-$C_8$ ether as defined above or a mixture thereof, depending on the reducing agent, at a temperature between 0° to 40° C., over a period of about 0.5 to 10 hours. When the catalyst Pd/C, $PtO_2$ or $PdCl_2$ is used, the $H_2$ pressure is typically 1 atmosphere. When Raney nickel is used, the $H_2$ pressure is moderately high (~1000 psi). Typically, the hydrogenation is carried out over a period of about 5 to about 24 hours.

When the reduction is carried out upon catalytic transfer hydrogenation (CTH) conditions, suitable hydrogen-bearing feed materials, such as, for example formic acid, ammonium formate or sodium formate, preferably ammonium formate or sodium formate are employed. In order to activate the hydrogen-bearing material as hydrogen donor, a catalyst as defined above is employed: the catalyst promotes the hydrogen transfer from hydrogen-bearing feed material to the substrate. CTH may be performed by any method known to a person skilled in the art. In particular, when CTH techniques are used in the reaction under step e), the compound of formula (V) is dissolved in a solvent selected from for example, toluene, acetic acid and a $C_1$-$C_5$ alcohol as defined above, preferably ethyl alcohol, in the presence of formic acid, ammonium formate or sodium formate, preferably ammonium formate or sodium formate, at refluxing temperature of the selected solvent, over a period of about 5 to 48 hours.

The compound of formula (Va) can then be used for preparing Cinacalcet.

In another embodiment, the present invention encompasses a process for preparing Cinacalcet, by preparing a compound of formula (Va) as described above, and converting it to Cinacalcet.

In another embodiment, the present invention provides the preparation of a Cinacalcet intermediate of formula (VI)

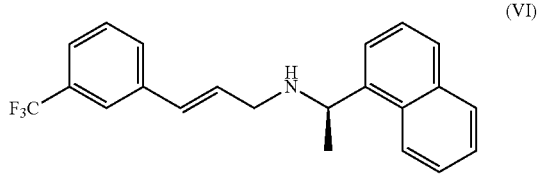 [SMILES: C[C@@H](NC/C=C/c1cccc(C(F)(F)F)c1)c1cccc2ccccc12]

which comprises the step of:
f) dehydrating a compound of formula (Va) with a dehydrating agent; or, alternatively,
g) reducing the compound of formula (V) as defined above with Zn, in the presence of an acid, so obtaining the compound of formula (VI), in a mixture with Cinacalcet of formula (I).

The reaction under step f) can be carried out with suitable dehydrating agents selected from, for example sulfuric acid, phosphoric acid, acetic anhydride, $PCl_5$, toluic acid, camphorsulfonic acid and tosylic acid, at a temperature between 40° to 130° C., with or without a solvent selected from, for example toluene, acetic acid and mixture thereof, over a period of about 1 to 48 hours.

The reduction under step g) can be carried out in the presence of zinc powder, in an acidic medium, with the acid selected from, for example HBr and HCl, preferably HCl, in a solvent selected from, for example water, a $C_1$-$C_5$ alcohol as defined above, toluene and acetonitrile; preferably, the reduction is carried out in a mixture of methanol and water, at a temperature between 25° to 80° C., over a period of about 1 to 48 hours. Both Cinacalcet of formula (I) and the corresponding unsaturated derivative of formula (VI) are obtained from the reaction under step g). Typically, the compound of formula (VI) is recovered from the reaction by 8:1 to 1:8 HPLC ratio. In a preferred aspect, the compound of formula (VI) is recovered from the reaction mixture in 2 to 1 ratio, using a 1:1 methanol/water mixture with an excess of zinc, operating at a temperature of 25° C.

The compound of formula (VI) can then be used for preparing Cinacalcet.

In another embodiment, the present invention encompasses a process for preparing Cinacalcet, by preparing a compound of formula (VI) as described above, and converting it to Cinacalcet.

The present invention further provides the preparation of Cinacalcet of formula (I) as defined above, which comprises the step of:
h) reducing the double bond of the compound of formula (VI) to obtain the compound of formula (I).

The reduction of the compound of formula (VI) under step h) can be carried out by catalytic hydrogenation, i.e. with molecular hydrogen in the presence of a catalyst or, alternatively, by catalytic transfer hydrogenation (CTH), i.e with hydrogen released by a hydrogen-bearing material in the presence of a catalyst. CTH may be performed by any method known to a person skilled in the art. For example, the unsaturated Cinacalcet of formula (VI) may be dissolved in a $C_1$-$C_5$ alcohol as defined above and exposed to $H_2$ pressure, in the presence of a catalyst such as, for example Pd/C, $PtO_2$ (Adam's catalysts), Raney nickel or $PdCl_2$. When Pd/C, $PtO_2$ or $PdCl_2$ is used, the $H_2$ pressure is typically 1 atmosphere. When Raney nickel is used, the $H_2$ pressure is moderately high (~1000 psi). Typically, the hydrogenation is carried out over a period of about 5 to about 24 hours. When CTH reaction conditions are performed, the compound of formula (VI) is dissolved in a solvent selected from for example, toluene, acetic acid and a $C_1$-$C_5$ alcohol as defined above, in the presence of formic acid, ammonium formate or sodium formate, preferably ammonium formate or sodium formate, at refluxing temperature of the selected solvent, over a period of about 5 to 48 hours.

The above steps can be combined to obtain a continuous process ending in Cinacalcet of formula (I).

This process, when utilizing the above steps a), e), f) and h), comprises preparing Cinacalcet of formula (I)

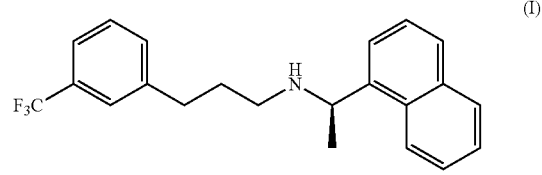 [SMILES: C[C@@H](NCCCc1cccc(C(F)(F)F)c1)c1cccc2ccccc12]

which comprises the steps of:
a) reacting 3-(trifluoromethyl)acetophenone of formula (II)

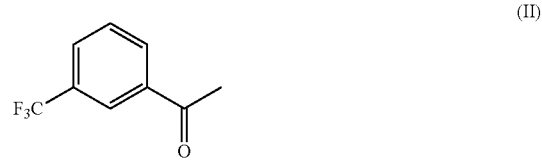

with (R)-(1-naphthyl)ethylamine of formula (III)

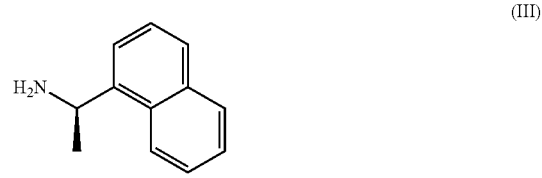

in the presence of formaldehyde, to give the compound of formula (V)

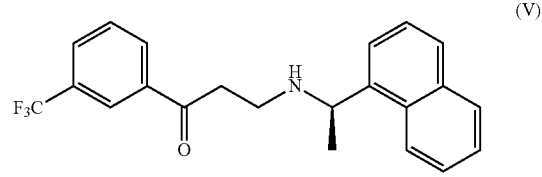 [SMILES: C[C@@H](NCCC(=O)c1cccc(C(F)(F)F)c1)c1cccc2ccccc12]

e) reducing the compound of formula (V) in the presence of a reducing agent or by mean of a catalytic hydrogenation process to give a compound of formula (Va)

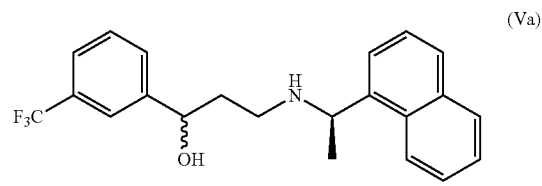 [SMILES: C[C@@H](NCCC(O)c1cccc(C(F)(F)F)c1)c1cccc2ccccc12]

f) dehydrating a compound of formula (Va) with a dehydrating agent to give a compound of formula (VI)

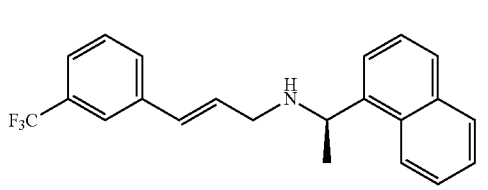
(VI)

and h) reducing the compound of formula (VI) to give Cinacalcet of formula (I).

This process, when utilizing the above steps a), g) and h), comprises preparing Cinacalcet of formula (I)

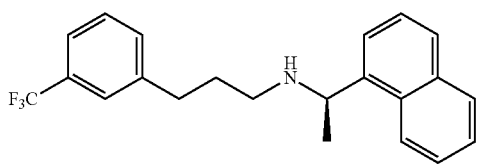
(I)

which comprises the steps of:
a) reacting 3-(trifluoromethyl)acetophenone of formula (II)

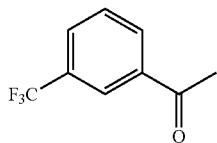
(II)

with (R)-(1-naphthyl)ethylamine of formula (III)

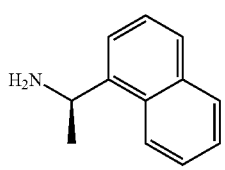
(III)

in the presence of formaldehyde, to give the compound of formula (V)

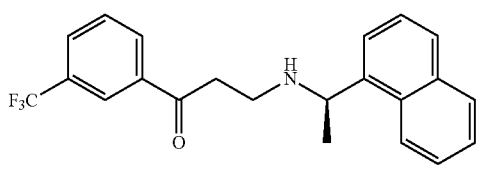
(V)

g) reducing the compound of formula (V) as defined above with Zn, in the presence of an acid, so obtaining the compound of formula (VI)

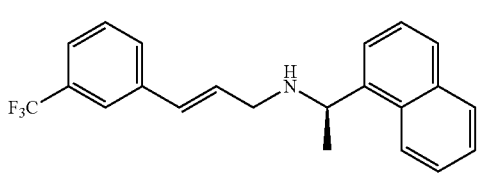
(VI)

in admixture with Cinacalcet of formula (I); and
h) reducing the compound of formula (VI) to give Cinacalcet of formula (I).

This process, when utilizing the above steps b), c) d), e) f) and h), comprises preparing Cinacalcet of formula (I).

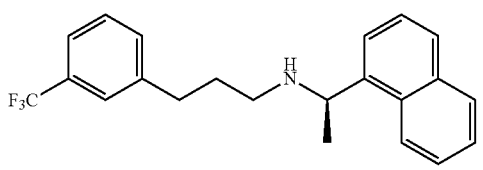
(I)

which comprises the steps of:
b) reacting the compound of formula (II) as defined above
  (i) with a compound of formula $HNR_1R_2$, wherein $R_1$ and $R_2$ represent, independently, hydrogen or $C_1$-$C_5$ alkyl, provided that when one of $R_1$ and $R_2$ is hydrogen, the other is not hydrogen; or wherein $R_1$ and $R_2$ together form a $C_4$-$C_7$-alkylene bridge, so that with the inclusion of the nitrogen atom to which they are linked a heterocycle is formed, wherein one —$CH_2$— group of the $C_4$-$C_7$-alkylene bridge, can be replaced by —O—, in the presence of formaldehyde; or
  (ii) with a N-methyl-N-methylenemethanaminium halide of formula

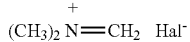

wherein Hal is a halogen atom,
   to obtain the compound of formula (IV)

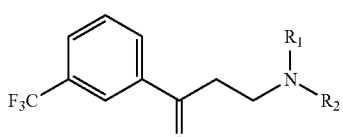
(IV)

wherein $R_1$ and $R_2$ are as defined above;
c) alkylating the compound of formula (IV) with an alkylating agent selected from the group of compounds of formula: $R_3$—X, $CO(OR_3)_2$, $SO_2(OR_3)_2$, $PO(OR_3)_3$, $CH_3PO(OR_3)_2$ and $(4\text{-}NO_2C_6H_4O)PO(OR_3)_2$, wherein $R_3$ is $C_1$-$C_4$alkyl and X is I, Br, $OSO_2CF_3$ or $OSO_2F$, to obtain a compound of formula (IVa)

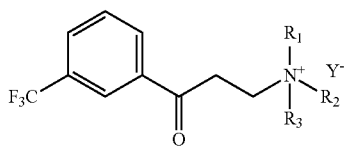

wherein Y=X as defined above, R₃OCO₂, R₃OSO₃, (R₃O)₂PO₂, CH₃PO₂OR₃, or (4-NO₂—C₆H₄O)PO₂OR₃;

d) coupling a compound of formula (IVa) with (R)-(1-naphthyl)ethylamine of formula (III) to give the compound of formula (V)

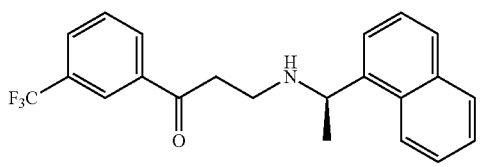

e) reducing the compound of formula (V) in the presence of a reducing agent or by mean of a catalytic hydrogenation process to give a compound of formula (Va)

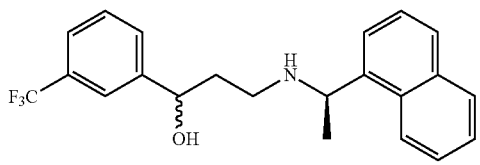

f) dehydrating a compound of formula (Va) with a dehydrating agent to give a compound of formula (VI)

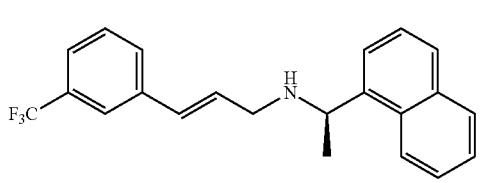

and h) reducing the compound of formula (VI) to give Cinacalcet of formula (I).

This process, when utilizing the above steps b), c) d), g) and h), comprises preparing Cinacalcet of formula (I)

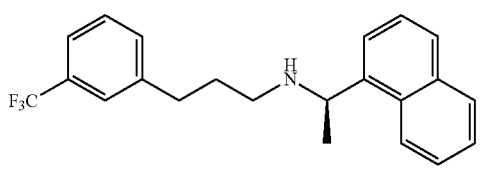

which comprises the steps of:

b) reacting the compound of formula (II) as defined above
  (i) with a compound of formula
    HNR₁R₂,
    wherein R₁ and R₂ represent, independently, hydrogen or C₁-C₅ alkyl, provided that when one of R₁ and R₂ is hydrogen, the other is not hydrogen; or wherein R₁ and R₂ together form a C₄-C₇-alkylene bridge, so that with the inclusion of the nitrogen atom to which they are linked a heterocycle is formed, wherein one —CH₂— group of the C₄-C₇-alkylene bridge, can be replaced by —O—, in the presence of formaldehyde; or
  (ii) with a N-methyl-N-methylenemethanaminium halide of formula

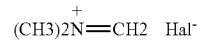

wherein Hal is a halogen atom,
    to obtain the compound of formula (IV)

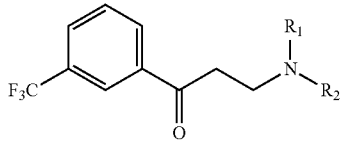

wherein R₁ and R₂ are as defined above;

c) alkylating the compound of formula (IV) with an alkylating agent selected from the group of compounds of formula: R₃—X, CO(OR₃)₂, SO₂(OR₃)₂, PO(OR₃)₃, CH₃PO(OR₃)₂ and (4-NO₂C₆H₄O)PO(OR₃)₂, wherein R₃ is C₁-C₄alkyl and X is I, Br, OSO₂CF₃ or OSO₂F, to obtain a compound of formula (IVa)

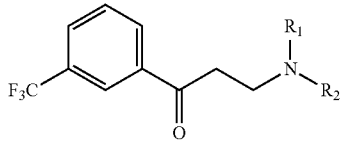

wherein Y=X as defined above, R₃OCO₂, R₃OSO₃, (R₃O)₂PO₂, CH₃PO₂OR₃ or (4-NO₂—C₆H₄O)PO₂OR₃;

d) coupling a compound of formula (IVa) with (R)-(1-naphthyl)ethylamine of formula (III) to give the compound of formula (V)

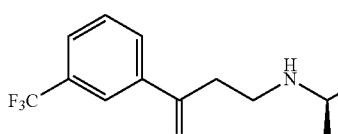

g) reducing the compound of formula (V) as defined above with Zn, in the presence of an acid, so obtaining the compound of formula (VI)

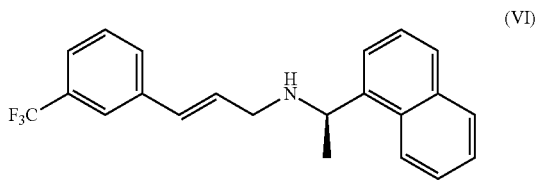 [SMILES: C[C@@H](NC/C=C/c1cccc(C(F)(F)F)c1)c1cccc2ccccc12]

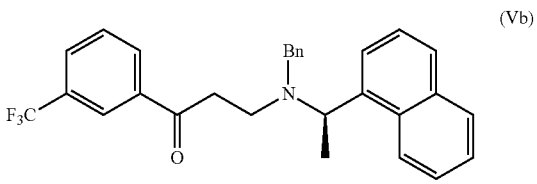

in admixture with Cinacalcet of formula (I); and h) reducing the double bond of the compound of formula (VI) to obtain the compound of formula (I).

If desired, the compound of formula (I) is reacted with a pharmaceutically acceptable acid suitable to form a pharmaceutically acceptable salt thereof.

Suitable pharmaceutically acceptable acids, which can be used to form Cinacalcet salts can be, for example HCl, HBr, $H_2SO_4$, maleic acid and fumaric acid, preferably HCl.

Cinacalcet may be converted into a pharmaceutically acceptable Cinacalcet salt by any method known to a person skilled in the art. A preferred pharmaceutically acceptable salt is the hydrochloride salt. For example, the hydrochloride salt may be prepared by a method which comprises reacting Cinacalcet with hydrogen chloride. Typically, Cinacalcet base is dissolved in an organic solvent and combined with aqueous or gaseous hydrogen chloride to obtain Cinacalcet hydrochloride. Preferably, the organic solvent is toluene or ethyl acetate or MTBE.

The starting materials of formula (II) and (III) are commercially available compounds or can be prepared according to the literature available in the prior art. For example, 3-(trifluoromethyl)acetophenone of formula (II) can be prepared following the procedure disclosed in the U.S. Pat. No. 6,420,608.

It is another object of the present invention the Cinacalcet intermediate of formula (V)

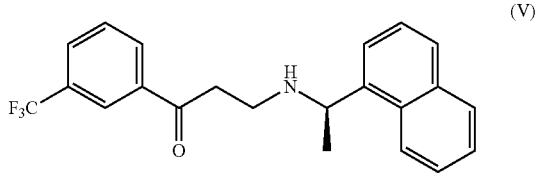 [SMILES: C[C@@H](NCCC(=O)c1cccc(C(F)(F)F)c1)c1cccc2ccccc12]

It is still another object of the present invention a Cinacalcet intermediate of formula (Va)

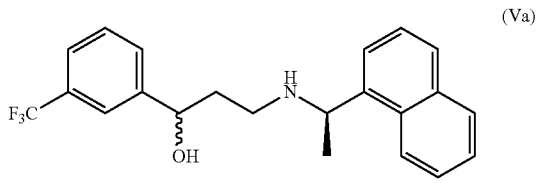 [SMILES: C[C@@H](NCCC(O)c1cccc(C(F)(F)F)c1)c1cccc2ccccc12]

which is a diastereoisomeric mixture of (R)- and (S)-3-((R)-1-(naphtalen-1-yl)ethylamino-1-(3-(trifluoromethyl)phenyl)propan-1-ol.

According with a further aspect of the present invention, it is provided the preparation of a Cinacalcet intermediate of formula (Vb)

wherein Bn is benzyl, which comprises the step of:

j) coupling compound of formula (IVa) as defined above, with (R)—N-benzyl-1-(1-naphthyl)ethylamine of formula (IIIa)

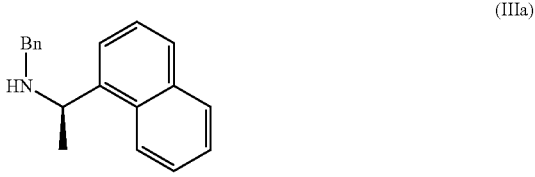

wherein Bn is as defined above.

The compound of formula (Vb) can then be used for preparing Cinacalcet.

In another embodiment, the present invention encompasses a process for preparing Cinacalcet, by preparing a compound of formula (Vb) as described above, and converting it to Cinacalcet.

In another embodiment, the present invention provides the preparation of Cinacalcet of formula (I) which comprises the step of:

k) reducing the compound of formula (Vb) to Cinacalcet of formula (I), and, if desired, reacting Cinacalcet of formula (I) with a pharmaceutically acceptable acid suitable to form a salt with the compound of formula (I).

According to this aspect of the invention the alkylated Mannich base (IVa) is coupled with N-benzyl-(R)-NEA of formula (IIIa) under step j), upon analogous conditions used for coupling said alkylated Mannich base with (R)-(1-naphthyl) ethylamine of formula (III) previously reported under step d). The reaction can be carried out in the presence or not of a base that can be, for example calcium carbonate, potassium carbonate or triethylamine, preferably sodium carbonate, in a solvent selected from EtOAc, dimethylformamide, acetonitrile and toluene, preferably acetonitrile or toluene, and more preferably toluene, at a temperature between 0° to 80° C. over a period of about 2 to 24 hours.

It is another object of the present invention the Cinacalcet intermediate of formula (Vb)

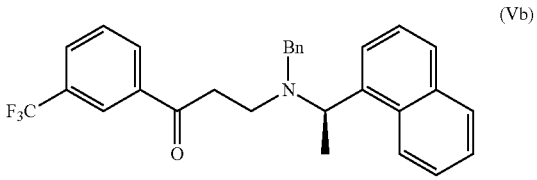

wherein Bn is benzyl.

N-benzyl-(R)-NEA hydrochloride of formula (Ma), either purchased from commercial sources or prepared on purpose via trivial synthetic steps, is converted into the free base before being coupled to the alkylated Mannich base of formula (IVa) by neutralization with an aqueous base selected among sodium hydroxide, potassium or calcium carbonate, preferably with aqueous sodium hydroxide, and extracted with a water-immiscible organic solvent chosen from a $C_4$-$C_8$ linear or cyclic aliphatic ether as defined above, aliphatic or aromatic hydrocarbons as defined above, preferably toluene, at a temperature ranging from 10° to 40° C., preferably 25° C.

The reduction of the compound of formula (Vb) under step k) can be achieved thorough a combined carbonyl deoxygenation/N-debenzylation carried out upon standard catalytic hydrogenation condition, i.e. with molecular hydrogen in the presence of catalyst, to obtain Cinacalcet of formula (I). The catalytic hydrogenation may be performed by any method known to a person skilled in the art. For example, the intermediate of formula (Va) may be dissolved in a $C_1$-$C_4$ alcohol as defined above, and subjected to $H_2$ pressure in the presence of a catalyst such as Pd/C or $PtO_2$.

When Pd/C or $PtO_2$ is used, the $H_2$ pressure is typically 1 atmosphere. Typically, the hydrogenation is carried out over a period of about 5 to about 24 hours.

The present invention is exemplified by the following examples, which are provided for illustration only and should not be construed to limit the scope of the invention.

EXAMPLE 1

Synthesis of (R)-3-(1-(naphthalen-1-yl)ethylamino)-1-(3-(trifluoromethyl)phenyl)propan-1-one hydrochloride salt (V)

Method A

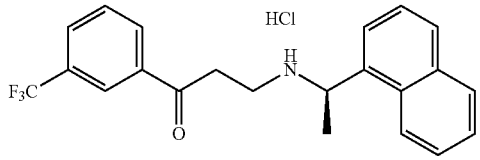 [SMILES: C[C@@H](NCCC(=O)c1cccc(C(F)(F)F)c1)c1cccc2ccccc12 ; Cl]

(R)-(1-naphthyl)ethylamine hydrochloride (III) (100.0 g), paraformaldehyde (15.9 g), 3-(trifluoromethyl)acetophenone (II) (135.7 g), 30% w/w aqueous hydrochloric acid (5.6 g), ethanol (150.0 g) and water (10.0 g) were charged into the reactor and stirred at reflux for 14 hrs, until satisfactory conversion was observed via HPLC. Then water (300.0 g) and toluene (305.0 g) were added and the mixture was stirred at 25° C. The organic and aqueous layers were separated and additional water (200.0 g) was charged over the organic phase in order to favour the precipitation. The title compound (95.6 g) was isolated upon filtration at room temperature, washing with water and methyl tert-butyl ether and exsiccation at 50° C.

NMR of R)-3-(1-(naphthalen-1-yl)ethylamino)-1-(3-(trifluoromethyl)-phenyl)-propan-1-one hydrochloride salt (V)

$^1$H NMR (400 MHz, DMSO-$d_6$), δ (ppm, TMS): 10.00 (1H, br s; —$NH_2^+$—), 9.24 (1H, br s; —$NH_2^+$—), 8.31 (1H, d, J=8.4; ArH), 8.23 (1H, d, J=8.0 Hz; ArH), 8.16 (1H, br s; ArH), 8.08-7.96 (4H, m; ArH), 7.82 (1H, t, J=8.0 Hz; ArH), 7.69-7.58 (3H, m; ArH), 5.47-5.36 (1H, m; —CH($CH_3$)—), 3.70-3.54 (2H, m; —$CH_2$—), 3.41-3.26 (2H, m; —$CH_2$—), 1.72 (3H, m, J=6.4 Hz; —CH($CH_3$)—).

Method B (R)-(1-naphthyl)ethylamine hydrochloride (III) (1.5 g), paraformaldehyde (0.3 g), 3-(trifluoromethyl)acetophenone (II) (1.8 g), 30% w/w aqueous hydrochloric acid (0.1 g), ethanol (4.5 g) and water (1.5 g) were charged into the reactor under stirring and reacted for 5 minutes under microwave irradiation (max 250 W), until satisfactory conversion was observed via HPLC. Then water (10.0 g) and toluene (3.0 g) were added and the resulting suspension was stirred at 25° C. The title compound (1.6 g) was isolated upon filtration at room temperature, washing with water and methyl 2-propanol and exsiccation at 50° C.

EXAMPLE 2

Synthesis of 3-(dimethylamino)-1-(3-(trifluoromethyl)phenyl)propan-1-one hydrochloride (IV)

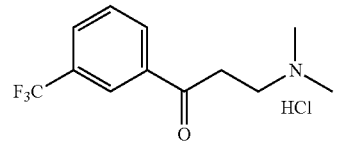 [SMILES: CN(C)CCC(=O)c1cccc(C(F)(F)F)c1 ; Cl]

A mixture of 1-(3-(trifluoromethyl)phenyl)ethanone (25.0 g) (II), dimethylamine hydrochloride (13.0 g), paraformaldehyde (4.8 g), 31% w/w aqueous hydrochloric acid (0.5 mL) in ethanol (70 mL) was stirred at reflux temperature for 24 hrs, then cooled down and the solvent flushed with toluene (50 mL). The precipitated pale yellow solid was then filtrated, washed with toluene and dried to give the title compound (IV) (28.0 g).

EXAMPLE 3

Synthesis of 3-(dimethylamino)-1-(3-(trifluoromethyl)phenyl)propan-1-one hydroiodide (IV)

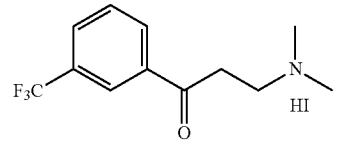

A mixture of 1-(3-(trifluoromethyl)phenyl)ethanone (5.0 g) (II), N-methyl-N-methylenemethanaminium iodide (5.4 g), 31% w/w aqueous hydrochloric acid (0.1 mL) in ethanol (7 mL) was stirred at reflux temperature for 24 hrs, then cooled down and the solvent flushed with toluene (50 mL). The precipitated pale yellow solid was then filtrated, washed with toluene and dried to give the title compound (IV) (7.1 g).

EXAMPLE 4

Synthesis of N,N,N-trimethyl-3-oxo-3-(3-(trifluoromethyl)phenyl)propan-1-aminium iodide (IVa)

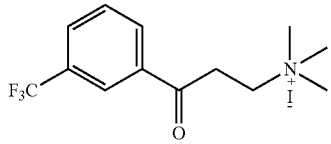

A vigorously stirred biphasic solution of 3-(dimethylamino)-1-(3-(trifluoromethyl)phenyl)propan-1-one (IV) (15.0 g) in a 1:1 water/toluene mixture (50 mL) was added over 1 hr at r.t. with 30% w/w aqueous sodium hydroxide until pH 14. The organic layer was then separated, dried with anhydrous $Na_2SO_4$ and filtered. The mother liquor was then charged in a reactor and added, under strong agitation, with methyliodide (22.6 g) in 30 min. The mixture was then kept at r.t. for 18 hrs to yield a yellow solid of the methylated Mannich base iodide salt (18.0 g), compound (IVa), that was filtered, dried and used in the following synthetic step without further purification.

EXAMPLE 5

Synthesis of (R)-3-(1-(naphthalen-1-yl)ethylamino)-1-(3-(trifluoromethyl)phenyl)propan-1-one hydrochloride salt (V)

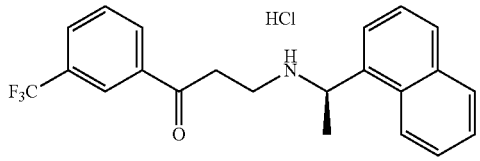 [SMILES: C[C@@H](NCCC(=O)c1cccc(C(F)(F)F)c1)c1cccc2ccccc12 ; Cl]

A vigorously stirred suspension of the methylated Mannich base iodide salt, compound (IVa) (20.5 g), (R)-(1-naphthyl)ethylamine (11.0 g) and potassium carbonate (14.7 g) in acetonitrile (50 mL) was kept at refluxing temperature for 8 hrs, then cooled down to r.t., added with water (20 mL) and extracted twice with ethyl acetate (25 mL). The combined organic phases were then dried and concentrated to give the crude title compound (V) (20.8 g) as yellow oil. Further purification could be achieved upon conversion of the compound (V) into its hydrochloride salt and recrystallization from MTBE.

EXAMPLE 6

Synthesis of a mixture of (R,E)-N-(1-(naphthalen-1-yl)ethyl)-3-(3-(trifluoromethyl)phenyl)prop-2-en-1-amine (VI) and (R)—N-(1-(naphtalen-1-yl)ethyl)-3-(3-(trifluoromethyl)phenyl)propan-1-amine (I)

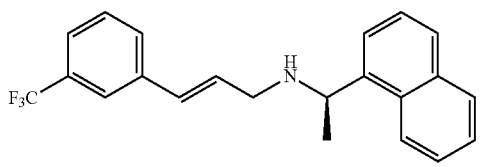 [SMILES: C[C@@H](NC/C=C/c1cccc(C(F)(F)F)c1)c1cccc2ccccc12]

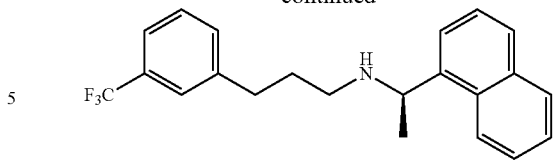

A suspension of compound (V) as its hydrochloride salt (3.0 g) and zinc powder (1.42 g) in a 1:1 methanol/water mixture (20 mL) at r.t., was added dropwise in 5 hrs with a 31% w/w solution of hydrochloric acid in water. The reaction mixture was then partially concentrated, diluted with toluene (50 mL) and the phases separated. The organic layer was then neutralized with 30% w/w aqueous sodium hydroxide, dried over anhydrous $Na_2SO_4$ and filtrated to obtain a yellow oil (2.5 g) as a mixture (2:1) of compound (VI) and Cinacalcet compound (I), that can be used in other synthetic steps without further purification.

EXAMPLE 7

Synthesis of (R)- and (S)-3-((R)-1-(naphtalen-1-yl)ethylamino-1-(3-(trifluoromethyl)phenyl)propan-1-ol (Va)

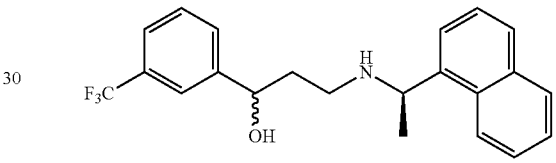

(R)-3-(1-(naphthalen-1-yl)ethylamino)-1-(3-(trifluoromethyl)phenyl)propan-1-one hydrochloride salt (V) (20.0 g) was suspended in methanol (61.9 g) at 5° C. and 30% w/w aqueous sodium hydroxide (6.8 g) was charged dropwise over 15 mins. The reaction mixture was stirred for 15 mins, then a solution of sodium borohydride (2.2 g) and aqueous soda (30% w/w; 0.7 g) in water (6.1 g) was added slowly. The suspension was stirred at 25° C. for 0.5 hrs, and, once the reaction went to completion (IPC via HPLC), toluene (84.9 g) and methanol (28.6 g) were charged. Solvents were distilled off to approximately half volume at 25°-30° C. under reduced pressure, the organic phase was separated and washed with brine. Combined aqueous layers were extracted with toluene (84.3 g) and the organic phases were distilled off to reduced volume at 50° C. (80-100 mbar). Either the resulting solution was used as such in the following step or the crude title product (Va) was isolated by further distilling off the solvent to residue.

EXAMPLE 8

Synthesis of (R,E)-N-(1-(naphthalen-1-yl)ethyl)-3-(3-(trifluoromethyl)phenyl)prop-2-en-1-amine (VI)

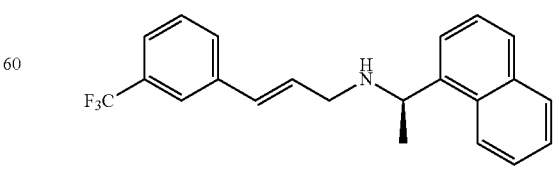

The diastereoisomeric mixture of (R) and (S)-3-((R)-1-(naphtalen-1-yl)ethylamino-1-(3-(trifluoromethyl)phenyl)

propan-1-ol was charged into the reactor as a toluene solution (33.7 g). Acetic acid (76.9 g) and concentrated sulphuric acid (96% w/w; 49.0 g) were then added slowly at 25° C., the reaction mixture was heated at 110° C. for 1 hr, then cooled down to 5° C. The mass was diluted by addition of toluene (85.0 g) and, dropwise, water (50.0 g), then stirred at 25° C. for few minutes. The organic and aqueous phases were separated and the toluene layer was cooled to 5° C. and neutralized by addition of aqueous ammonia (28% w/w; 40.0 g) up to pH 10. Once room temperature was reached, water (30.0 g) was added in order to solubilise salts, the phases were separated and the solvent was removed form the organic layer via reduced pressure distillation. The crude title compound (VI) was obtained as a pale yellow oil (17.7 g).

NMR of (R,E)-N-(1-(naphthalen-1-yl)ethyl)-3-(3-(trifluoromethyl)phenyl)prop-2-en-1-amine (VI)

$^1$H NMR (400 MHz, CDCl$_3$), δ (ppm, TMS): 8.21-8.17 (1H, m; ArH), 7.92-7.86 (1H, m; ArH), 7.78 (1H, d, J=8.0 Hz; ArH), 7.72 (1H, d, J=7.2 Hz; ArH), 7.58-7.45 (6H, m; ArH), 7.43-7.37 (1H, m; ArH), 6.48 (1H, d, J=16.0 Hz; —ArCH=CHCH$_2$—), 6.39 (1H, dt, J=16.0, 6.0 Hz; —ArCH=CHCH$_2$—), 4.76 (1H, q, J=6.6 Hz; —CH(CH$_3$)—), 3.46-3.33 (2H, m; —CH$_2$—), 1.57 (3H, d, J=6.6; —CH(CH$_3$)—).

EXAMPLE 9

Synthesis of Cinacalcet Free Base (I)

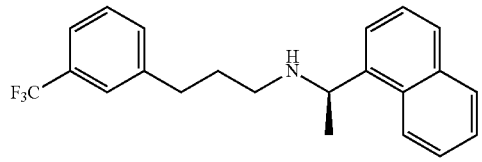 [SMILES: C[C@@H](NCCCc1cccc(C(F)(F)F)c1)c1cccc2ccccc12]

A mixture of compound (VI) (3.0 g), PdCl$_2$ (0.01 g) in ethanol (10 mL) was heated up to reflux temperature and added in 5 hrs with formic acid (0.3 g). The mixture was then cooled down, diluted with toluene and washed with 30% w/w aqueous sodium hydroxide until neutrality. The organic layer was dried and concentrated to give Cinacalcet free base, compound (I) (2.0 g).

EXAMPLE 10

Synthesis of Cinacalcet Free Base (I)

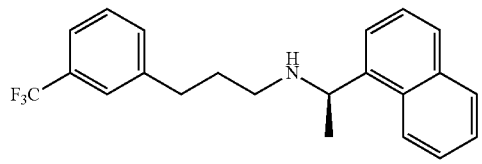 [SMILES: C[C@@H](NCCCc1cccc(C(F)(F)F)c1)c1cccc2ccccc12]

A mixture of compound (VI) (3.0 g), PdCl$_2$ (0.01 g), in methanol (10 mL) was pressurized with 1 bar hydrogen and stirred for 10 hrs at +25° C. The mixture was then filtered through a Celite® pad and concentrated to give Cinacalcet free base, compound (I) (2.0 g).

EXAMPLE 11

Synthesis of ((R)-3-(benzyl(1-(naphthalen-1-yl)ethyl)amino)-1-(3-(trifluoromethyl)phenyl)propan-1-one (Vb)

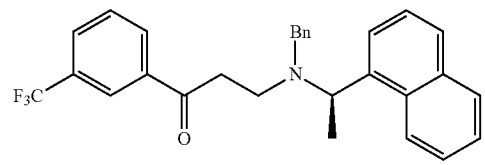 [SMILES: C[C@H](c1cccc2ccccc12)N(CCC(=O)c1cccc(C(F)(F)F)c1)Cc1ccccc1]

(R)—N-benzyl-1-(1-naphthyl)ethylamine hydrochloride (8.0 g), toluene (51.6 g), 30% w/w aqueous sodium hydroxide (20.4 g) and water (14.5 g) were charged into the reactor and stirred at r.t. for 0.5 hrs. The organic phase was separated and charged into the reactor over potassium carbonate (6.2 g). The mixture was then heated up to 80° C. and a suspension of methylated Mannich base iodide salt (IVa, where Alk=R$_1$=R$_2$=Me, Y=I) (7.0 g) in acetonitrile (76.4 g) was added dropwise over a period of 20 mins. The mass was stirred at 80° C. for 14 hrs, then water (60.0 g) was added and the two layers were separated. The organic layer was washed with 10% w/w aqueous hydrochloric acid (50.0 g) and the crude title compound (7.1 g) was obtained in the hydrochloride form as an off-white powder upon reduced pressure solvent removal. The free base was obtained by suspending the hydrochloride salt (7.1 g) in toluene (85.0 g) and water (46.0 g) and treating with 30% w/w aqueous sodium hydroxide (27.6 g) at r.t. Phase separation and solvent removal afforded the crude title compound (6.5 g) as a yellow oil.

NMR of ((R)-3-(benzyl(1-(naphthalen-1-yl)ethyl)amino)-1-(3-trifluoromethyl)-phenyl)propan-1-one (Vb)

$^1$H NMR (400 MHz, DMSO-d$_6$), δ (ppm, TMS): 8.19 (1H, d, J=8.4 Hz; ArH), 7.92-7.86 (3H, m; ArH), 7.86-7.83 (1H, m; ArH), 7.74 (1H, d, J=8.4 Hz; ArH), 7.64-7.56 (2H, m; ArH), 7.45-7.36 (3H, m; ArH), 7.20-7.19 (4H, m; ArH), 7.19-7.11 (1H, m; ArH), 4.69 (1H, q, J=6.8; —CH(CH$_3$)—), 3.73 (1H, d, J=14.0 Hz; PhCH$_2$—), 3.58 (1H, d, J=14.0 Hz; PhCH$_2$—), 3.24-3.01 (2H, m; —CH$_2$—), 3.00-2.89 (2H, m; —CH$_2$—), 1.48 (3H, d, J=6.8; —CH(CH$_3$)—).

The invention claimed is:
1. Cinacalcet intermediate having the following formula (V)

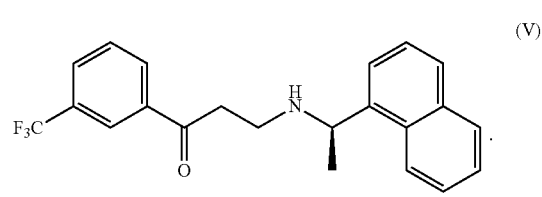 [SMILES: C[C@@H](NCCC(=O)c1cccc(C(F)(F)F)c1)c1cccc2ccccc12]

2. Cinacalcet intermediate having the following formula (Vb)

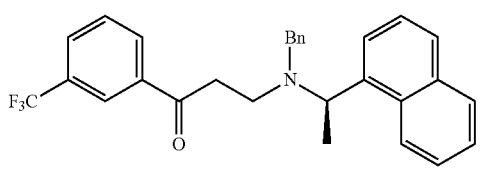

(Vb)

wherein Bn is benzyl.

3. A process for the preparation of Cinacalcet intermediate of formula (V),

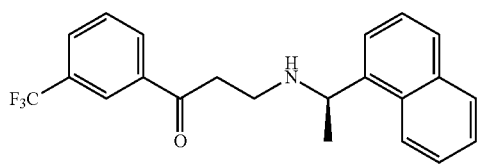

(V)

comprising the step of:
reacting 3-(trifluoromethyl)acetophenone of formula (II)

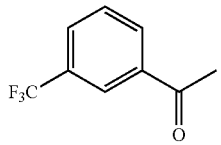

(II)

with (R)-(1-naphthyl)ethylamine of formula (III)

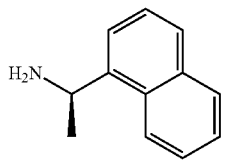

(III)

in the presence of formaldehyde, to give the compound of formula (V).

4. A process for the preparation of Cinacalcet intermediate of formula (V)

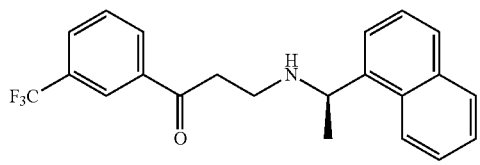

(V)

comprising the steps of:
reacting 3-(trifluoromethyl)acetophenone of formula (II)

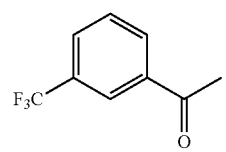

(II)

(i) with a compound of formula $HNR_1R_2$ wherein $R_1$ and $R_2$ represent, independently, hydrogen or $C_1$-$C_5$ alkyl, provided that when one of $R_1$ and $R_2$ is hydrogen, the other is not hydrogen; or wherein $R_1$ and $R_2$ together form a $C_4$-$C_7$-alkylene bridge, so that with the inclusion of the nitrogen atom to which they are linked form a heterocycle, wherein one —CH$_2$— group of the $C_4$-$C_7$-alkylene bridge, can be replaced by —O—, in the presence of formaldehyde; or (ii) with a N-methyl-N-methylenemethanaminium halide of formula

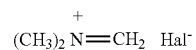

wherein Hal is a halogen atom,
to give the compound of formula (IV)

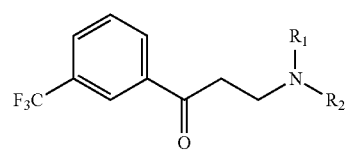

(IV)

wherein $R_1$ and $R_2$ are as defined above;
alkylating the compound of formula (IV) with an alkylating agent selected from the group of compounds of formula:

$R_3$—X, $CO(OR_3)_2$, $SO_2(OR_3)_2$, $PO(OR_3)_3$, $CH_3PO(OR_3)_2$ and $(4-NO_2C_6H_4O)PO(OR_3)_2$, wherein $R_3$ is $C_1$-$C_4$ alkyl and X is I, Br, $OSO_2CF_3$ or $OSO_2F$, to give a compound of formula (IVa)

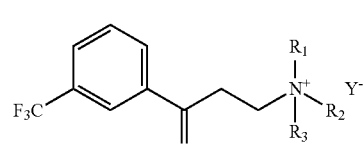

(IVa)

wherein Y=X as defined above or $R_3OCO_2$, $R_3OSO_3$, $(R_3O)_2PO_2$, $CH_3PO_2OR_3$, $(4-NO_2$—$C_6H_4O)PO_2OR_3$; and coupling a compound of formula (IVa) with (R)-(1-naphthyl)ethylamine of formula (III)

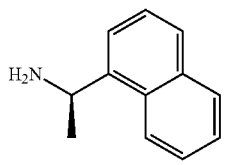

to give the compound of formula (V).

5. A process for preparing Cinacalcet of formula (I)

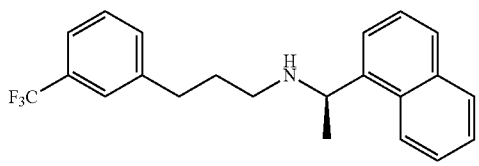

comprising preparing Cinacalcet intermediate of formula (V)

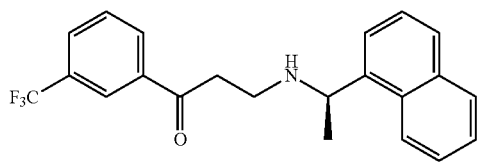

and converting it to Cinacalcet of formula (I).

6. A process for the preparation of Cinacalcet intermediate of formula (Va)

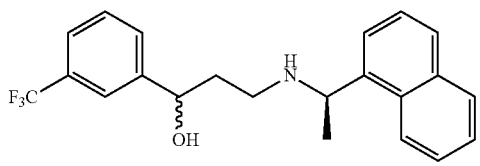

which comprises the step of:
reducing the compound of formula (V)

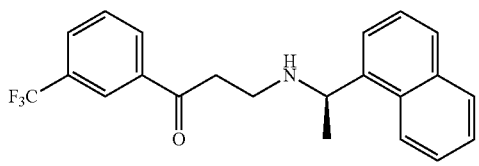

in the presence of a reducing agent or by mean of a catalytic hydrogenation process, to give the compound of formula (Va).

7. A process for preparing Cinacalcet of formula (I)

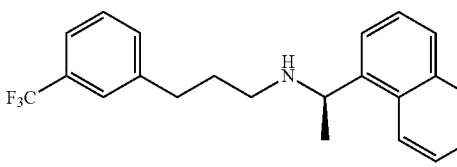

comprising preparing Cinacalcet intermediate of formula (Va)

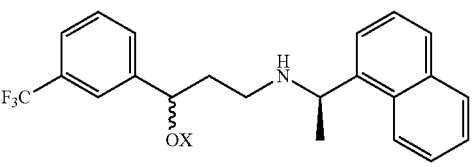

and converting it to Cinacalcet of formula (I).

8. A process for the preparation of a Cinacalcet intermediate of formula (VI)

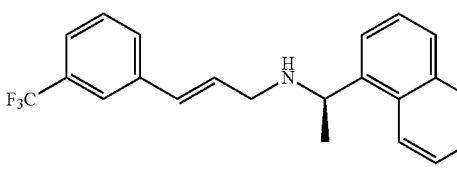

comprising:
dehydrating the compound of formula (Va)

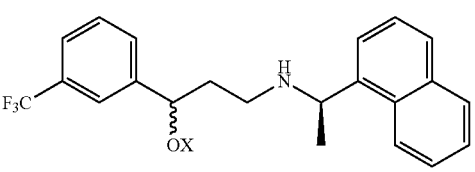

with a dehydrating agent so obtaining the compound of formula (VI).

9. A process for preparing Cinacalcet of formula (I)

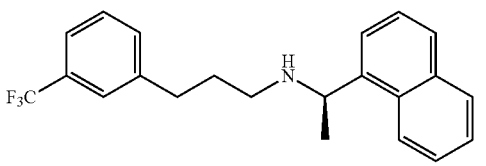

comprising preparing Cinacalcet intermediate of formula (VI)

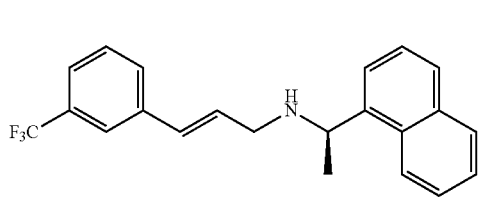
(VI)

and converting it to Cinacalcet of formula (I), by reducing the double bond of the compound of formula (VI)

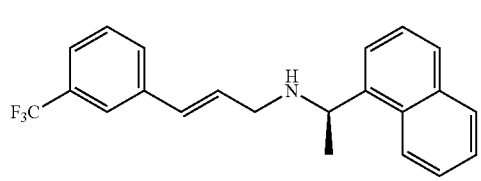
(VI)

to give Cinacalcet of formula (I).

10. A process for preparing Cinacalcet of formula (I)

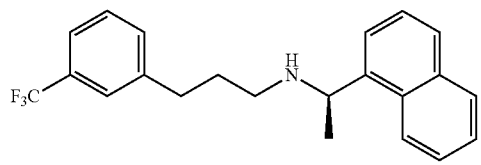
(I)

which comprises the steps of:

reacting 3-(trifluoromethyl)acetophenone of formula (II)

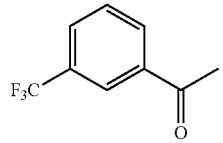
(II)

with (R)-(1-naphthyl)ethylamine of formula (III)

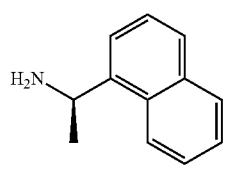
(III)

in the presence of formaldehyde, to give the compound of formula (V)

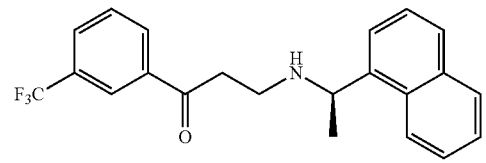
(V)

reducing the compound of formula (V) in the presence of a reducing agent or by mean of a catalytic hydrogenation process to give a compound of formula (Va)

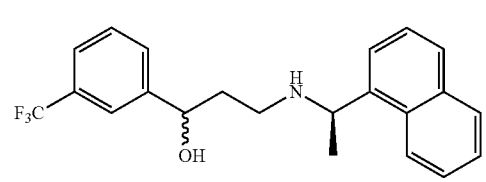
(Va)

dehydrating a compound of formula (Va) with a dehydrating agent to give a compound of formula (VI); and

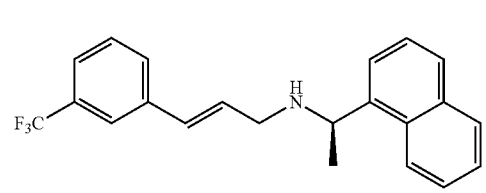
(VI)

reducing the compound of formula (VI), to give Cinacalcet of formula (I) and, if desired, converting Cinacalcet into a pharmaceutically acceptable salt.

11. A process for preparing Cinacalcet of formula (I)

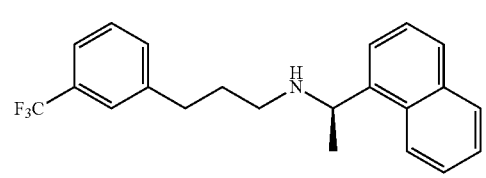
(I)

which comprises the steps of:

reacting 3-(trifluoromethyl)acetophenone of formula (II)

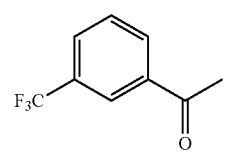
(II)

with (R)-(1-naphthyl)ethylamine of formula (III)

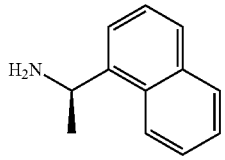
(III)

in the presence of formaldehyde, to give the compound of formula (V);

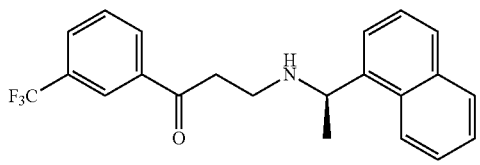
(V)

reducing the compound of formula (V) as defined above with Zn, in the presence of an acid, so obtaining the compound of formula (VI)

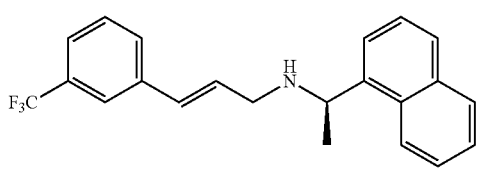
(VI)

in admixture with Cinacalcet of formula (I); and
reducing the compound of formula (VI), to give Cinacalcet of formula (I) and, if desired, converting Cinacalcet into a pharmaceutically acceptable salt.

12. A process for preparing Cinacalcet of formula (I)

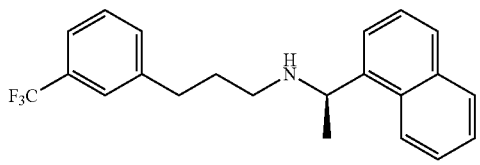
(I)

which comprises the steps of:
reacting the compound of formula (II)

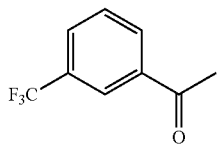
(II)

(i) with a compound of formula
HNR₁R₂, wherein $R_1$ and $R_2$ represent, independently, hydrogen or $C_1$-$C_5$ alkyl, provided that when one of $R_1$ and $R_2$ is hydrogen, the other is not hydrogen; or wherein $R_1$ and $R_2$ together form a $C_4$-$C_7$-alkylene bridge, so that with the inclusion of the nitrogen atom to which they are linked a heterocycle is formed, wherein one —CH₂— group of the $C_4$-$C_7$-alkylene bridge, can be replaced by —O—, in the presence of formaldehyde; or (ii) with a N-methyl-N-methylenemethanaminium halide of formula

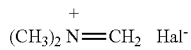

wherein Hal is a halogen atom,
to give the compound of formula (IV)

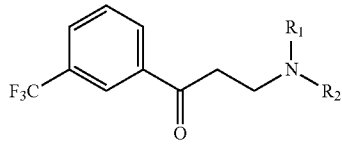
(IV)

wherein $R_1$ and $R_2$ are as defined above;
alkylating the compound of formula (IV) with an alkylating agent selected from the group of compounds of formula:

$R_3$—X, CO(OR₃)₂, SO₂(OR₃)₂, PO(OR₃)₃, CH₃PO(OR₃)₂ and (4-NO₂C₆H₄O)PO(OR₃)₂, wherein $R_3$ is $C_1$-$C_4$alkyl and X is I, Br, OSO₂CF₃ or OSO₂F, to obtain a compound of formula (IVa)

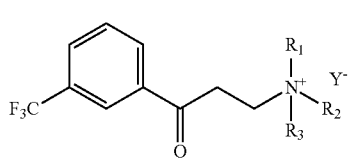
(IVa)

wherein Y=X as defined above, R₃OCO₂, R₃OSO₃, (R₃O)₂PO₂, CH₃PO₂OR₃, or (4-NO₂—C₆H₄O)PO₂OR₃;

coupling a compound of formula (IVa) with (R)-(1-naphthyl)ethylamine of formula (III) to give the compound of formula (V)

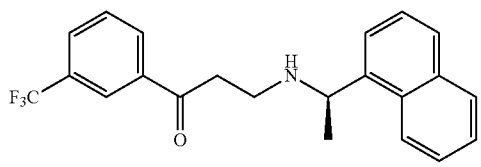
(V)

reducing the compound of formula (V) in the presence of a reducing agent or by mean of a catalytic hydrogenation process to give a compound of formula (Va)

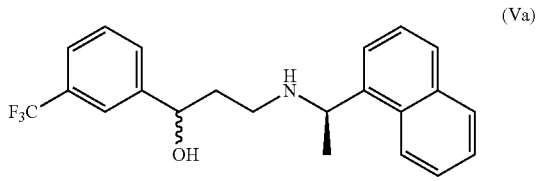 [SMILES: C[C@@H](NCCC(O)c1cccc(C(F)(F)F)c1)c1cccc2ccccc12]
(Va)

dehydrating a compound of formula (Va) with a dehydrating agent to give a compound of formula (VI); and

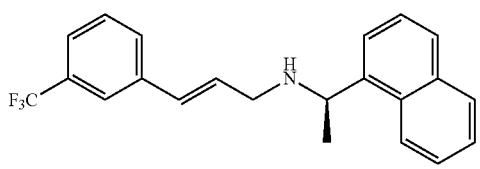
(VI)

reducing the compound of formula (VI), to give Cinacalcet of formula (I) and, if desired, converting Cinacalcet into a pharmaceutically acceptable salt.

13. A process for preparing Cinacalcet of formula (I)

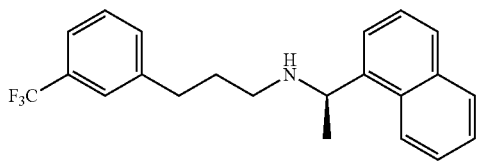
(I)

which comprises the steps of:

reacting the compound of formula (II) as defined above
(i) with a compound of formula $HNR_1R_2$, wherein $R_1$ and $R_2$ represent, independently, hydrogen or $C_1$-$C_5$ alkyl, provided that when one of $R_1$ and $R_2$ is hydrogen, the other is not hydrogen; or wherein $R_1$ and $R_2$ together form a $C_4$-$C_7$-alkylene bridge, so that with the inclusion of the nitrogen atom to which they are linked a heterocycle is formed, wherein one —$CH_2$— group of the $C_4$-$C_7$-alkylene bridge, can be replaced by —O—, in the presence of formaldehyde; or (ii) with a N-methyl-N-methylenemethanaminium halide of formula

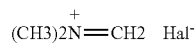

wherein Hal is a halogen atom, to obtain the compound of formula (IV)

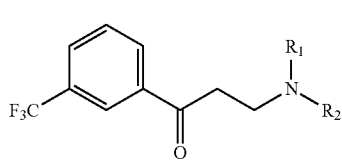
(IV)

wherein $R_1$ and $R_2$ are as defined above;

alkylating the compound of formula (IV) with an alkylating agent selected from the group of compounds of formula:

$R_3$—X, $CO(OR_3)_2$, $SO_2(OR_3)_2$, $PO(OR_3)_3$, $CH_3PO(OR_3)_2$ and $(4-NO_2C_6H_4O)PO(OR_3)_2$, wherein $R_3$ is $C_1$-$C_4$alkyl and X is I, Br, $OSO_2CF_3$ or $OSO_2F$, to obtain a compound of formula (IVa)

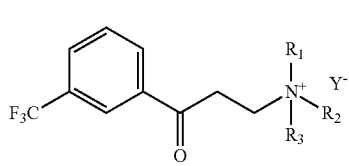
(IVa)

wherein Y=X as defined above, $R_3OCO_2$, $R_3OSO_3$, $(R_3O)_2PO_2$, $CH_3PO_2OR_3$ or $(4-NO_2$—$C_6H_4O)PO_2OR_3$;

coupling a compound of formula (IVa) with (R)-(1-naphthyl)ethylamine of formula (III) to give the compound of formula (V)

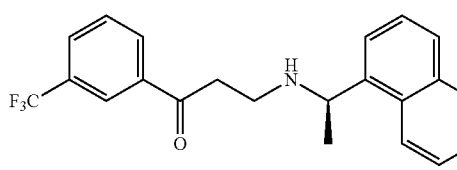
(V)

reducing the compound of formula (V) as defined above with Zn, in the presence of an acid, so obtaining the compound of formula (VI)

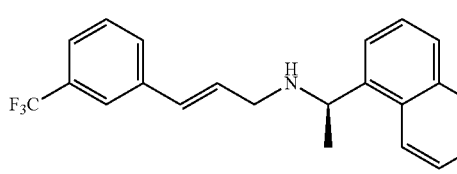
(VI)

in admixture with Cinacalcet of formula (I); and reducing the double bond of the compound of formula (VI), to give Cinacalcet of formula (I) and, if desired, converting Cinacalcet into a pharmaceutically acceptable salt.

14. A process for the preparation of Cinacalcet intermediate of formula (VI)
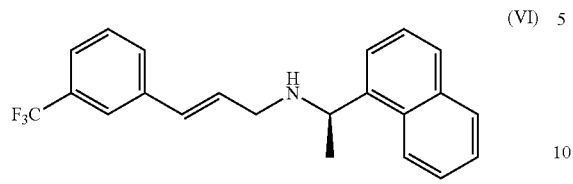
comprising reducing the compound of formula (V)
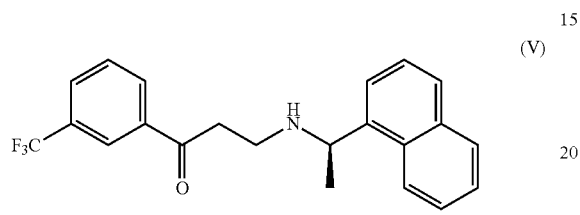
with Zn, in the presence of an acid, so obtaining the compound of formula (VI) in admixture with Cinacalcet of formula (I).
* * * * *